United States Patent [19]

Tureaud et al.

[11] 4,227,877
[45] Oct. 14, 1980

[54] ANATOMICAL INTRA-ORALLY MOLDABLE DENTAL IMPRESSION TRAY AND METHOD

[75] Inventors: Kenneth E. Tureaud; Stephen Ginsburg, both of Ann Arbor; Frederick Draheim, Orchard Lake, all of Mich.

[73] Assignee: Black Knight Investments, Limited, Grand Cayman, Cayman Islands

[21] Appl. No.: 843,443

[22] Filed: Oct. 20, 1977

Related U.S. Application Data

[63] Continuation-in-part of Ser. No. 754,107, Dec. 27, 1976, abandoned.

[51] Int. Cl.² ............................................. A61C 9/00
[52] U.S. Cl. ........................................ 433/37; 433/41
[58] Field of Search ................ 32/17, 2; 128/136; 433/37, 38, 41, 43, 48

[56] References Cited

U.S. PATENT DOCUMENTS

| | | | |
|---|---|---|---|
| 1,955,709 | 4/1934 | Kinsley | 32/17 |
| 2,577,513 | 12/1951 | Cunningham | 32/17 |
| 3,112,744 | 12/1963 | Grossberg | 128/136 |
| 3,224,441 | 12/1965 | Monaghan | 433/37 |
| 3,247,844 | 4/1966 | Berghash | 32/17 |
| 3,312,218 | 4/1967 | Jacobs | 433/37 |
| 3,473,225 | 10/1969 | Deuschle et al. | 32/17 |
| 3,839,796 | 10/1974 | Hazar | 32/2 |
| 3,864,832 | 2/1975 | Carlson | 128/136 |
| 3,924,638 | 12/1975 | Mann | 128/136 |
| 4,017,971 | 4/1977 | Hazar | 32/2 |

FOREIGN PATENT DOCUMENTS

| | | | |
|---|---|---|---|
| 468030 | 10/1928 | Fed. Rep. of Germany | 32/17 |
| 715041 | 11/1941 | Fed. Rep. of Germany | 32/17 |
| 885595 | 7/1949 | Fed. Rep. of Germany | 32/17 |
| 1297811 | 6/1969 | Fed. Rep. of Germany | 32/17 |

OTHER PUBLICATIONS

"Plastics Materials", 8-1966, Brydson, pp. 33, 34, 45, 46, 51, London Iliffe Books LTD.

*Primary Examiner*—Louis G. Mancene
*Assistant Examiner*—John J. Wilson
*Attorney, Agent, or Firm*—Krass & Young

[57] ABSTRACT

Dental impression trays, full, quadrant and anterior, shaped to closely conform to either the maxillary or mandibular ridges for either dentulous or edentulous cases have sections which anatomically approximate surrounding tissue areas with peripheral border relief for muscle attachments and contiguous tissue areas. The trays are formed of an acrylic having a glass transition temperature slightly above body temperature so that they may be heated above their softening temperature exteriorly of the oral cavity, positioned over the oral area of which an impression is to be made, and then manually molded to approximate intimate conformity to the desired oral structures before they harden. A pleat formed in the central vault of a maxillary tray accommodates transverse adjustment. When the tray cools and hardens it is removed, allowing a custom final impression to be thus formed in a single procedure.

23 Claims, 6 Drawing Figures

ANATOMICAL INTRA-ORALLY MOLDABLE DENTAL IMPRESSION TRAY AND METHOD

REFERENCE TO RELATED APPLICATION

This application is a Continuation-In-Part of U.S. Ser. No. 754,107, filed Dec. 27, 1976, now abandoned.

BACKGROUND OF THE INVENTION

1. Field of the Invention

This invention relates to anatomically shaped dental impression trays formed of thermoplastic material which may be directly molded within the mouth or on a male model and to a method of taking dental impressions of oral tissue, dental appliances, or dental prostheses using these trays.

2. Prior Art

To form a final impression of a dentulous or edentulous alveolar ridge, in the course of producing a male model of desired oral tissues, conventional practice involves the use of commercially available initial impression trays for use with either the maxillary or the mandibular alveolar ridges and contiguous tissues, in either dentulous or edentulous cases. These trays are available in a range of sizes so that one which makes an approximate fit with the patient's mouth area may be chosen for use. They have a cross-section characterized by a base with two normally extending walls so that they will surround the ridge of which an impression is to be formed. The contours of these trays are not anatomical in the sense that they are adapted to abut or lie in close proximity to the gum area surrounding the ridge, but rather a tray is chosen which fits within the patient's mouth and loosely surrounds the tooth or gum section. These stock trays are typically formed of aluminum or other material that may be bent or trimmed at the edges to improve the fit to an individual patient. Impression material is placed in the tray and a female cast of the required area is formed. This cast is then typically used to form a male model of the patient's mouth section either in the dental office or in a separate dental laboratory. The laboratory or dental office then uses this male model to form a custom final impression tray out of a plastic material. This tray is anatomical in that it closely adapts to the male model and is relieved in the muscle attachments and other contiguous tissue areas.

The dentist then uses this custom tray to form a final impression of the required area by placing a high definition, settable, impression material such as alginate, silicone, or polysulfide or the like, into the impression tray.

This conventional practice typically requires two procedures and is relatively expensive. Additionally, the stock impression tray may cause discomfort to the patient because of its relatively gross fit and inaccuracies creep into the procedure because of the multiple transfer steps.

A number of alternative means for forming final impressions have been proposed to overcome these recognized inadequacies of the conventional procedure. For example, several forms of stock trays have been devised which may be shaped exteriorly of the mouth to improve the accuracy of initial impressions. Deuschle et al U.S. Pat. No. 3,473,225 discloses such a stock tray formed of a thermoplastic sheet which can be heated exteriorly of the mouth and molded to improve its fit to the mouth. Similarly, McAdoo U.S. Pat. No. 3,654,703 discloses a stock tray made of plastic which is apparently pliable at body temperature and can be modified to better conform to the mouth.

Several arrangements have been proposed for elimination of the initial impressions altogether and formation of a final impression tray directly in the patient's mouth. Kinsley Pat. No. 1,955,709 discloses an impression tray formed of a woven metal matrix with a soft pliable covering that may be contoured directly to the patient's mouth. Similarly, German Pat. No. 885,772 discloses a process for making final impressions which does not use a tray for the impression material but rather employs an impression material which may be molded into a tray-like shape and then conformed to the mouth.

Each of these alternatives has certain deficiences. The non-anatomical trays which are moldable to better conform to the patient's intraoral anatomy still require formation of a male model and the creation of a final, anatomical impression tray using that model. The soft compliable final impression trays are susceptible to deformation as they are removed from the patient's mouth. The process suggested in the German patent suffers from the lack of the material which can form a self-supporting tray yet take a high definition registration of the tissue area.

SUMMARY OF THE INVENTION

The present invention is broadly directed toward final impression trays which may be formed in a single procedure like those of the Kinsley or McAdoo patents, yet are hardenable within the mouth so that when they are removed from the mouth they accurately retain their new configuration of approximate intimate conformity and do not become deformed. Moreover, the present invention is directed toward such a tray which is capable of accepting a high definition impression material for the formation of a final impression.

Impression trays of the present invention have a highly anatomical shape; that is, their contours and their margins are designed to closely conform to either a maxillary or a mandibular arch, either dentulous or edentulous alveolar ridge and/or dental appliances or prosthesis, with sections extending over the contiguous tissue areas and with relief for the fibrous tissue and muscle attachments. For example, the mandibular trays have extensions which cover the retromolar pad, and extend into the retromylohyoid fossae and cover the genial tubercles. Relief is provided for the anterior attachment of the mylohyoid muscle and for the buccal and labial freni. The maxillary version of the tray has a U-shaped, ridge engaging trough bordering a central vault engaging section having an axial pleat which allows lateral adjustment when softened. The tray thus closely conforms, in an anatomical sense, to the area of which the impression is to be made, as opposed to conventional stock trays which are substantially larger and minimal anatomical contouring or marginal relief.

The preferred embodiment of the tray, which will subsequently be disclosed in detail, has a handle extending from the convex side so that it may be easily inserted into and manipulated within the mouth. The tray also has tissue stops which comprise raised areas formed at spaced intervals on its concave surface. The tissue stops space the tray from the desired impression area to allow room for a proper thickness of a final impression material that will record the exact detail of the tissue.

In alternative embodiments the tray may have mechanical or chemical retentive devices or materials on its concave and/or convex side. These retentive devices or materials retain the final impression material. These may also act as tissue stops.

Trays of the present invention are formed of a thermoplastic which has a glass transition temperature above body temperature but below a temperature that will harm the oral tissues so that they may be heated above this softening temperature externally of the mouth and then placed within the mouth, over the impression area, and manually molded to provide approximate intimate conformity with the impression area. The glass transition temperature may range from 100° F. to 135° F. depending upon the exact plastic composition and the temperature at which they are placed in the mouth, this molding and adjustment of the pleat in the maxillary tray, may proceed for as long as two minutes before the tray will have cooled down below its transition temperature. It will then be rigid and self-supporting and may be removed from the mouth without significant loss of shape. The plastics are formulated so they have no appreciable memory; i.e., tendency to return to a previous shape.

The preferred embodiment of the invention is formed of an acrylic and more specifically a polymer formed of a copolymer of methylmethacrylate and monomethylmethacrylate is preferably employed. This material has a glass transition temperature of about 105° F.

Other objectives, advantages and applications of the present invention will be made apparent by the following detailed description of several embodiments. The description makes reference to the accompanying drawings in which.

Figure 1:
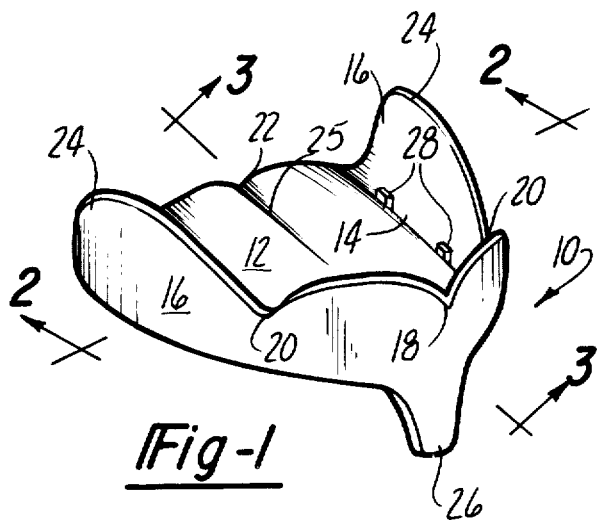
FIG. 1 is a perspective view of a maxillary impression tray formed in accordance with a preferred embodiment of the invention.
Figure 2:
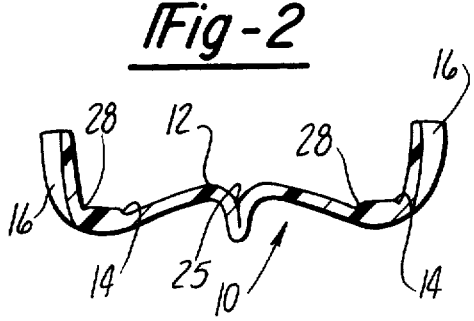
FIG. 2 is a transverse sectional view through the tray of FIG. 1, taken along line 2—2 of FIG. 1.
Figure 3:
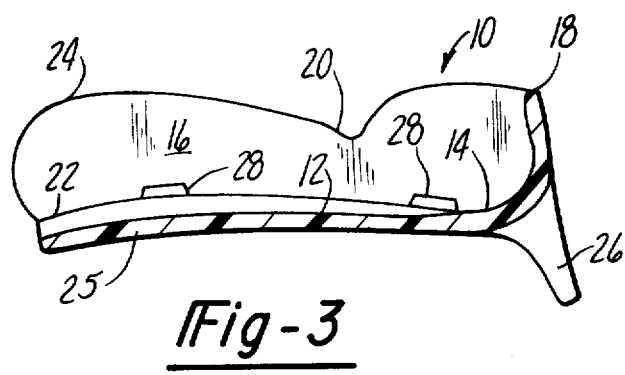
FIG. 3 is a longitudinal sectional view through the tray of FIG. 1, taken along lines 3—3 of FIG. 1.

A maxillary impression tray, generally indicated at 10 in FIGS. 1 through 3, is shaped to make a close anatomical fit with an edentulous maxillary alveolar ridge and palatal vault. In commercial practice, stock trays would be made available in a graduation of sizes and a similar series of dentulous trays would be provided so that a dentist could select a tray which relatively closely conforms to a particular case.

The tray 10 is contoured in a three-dimensional manner to closely conform to the anatomy of the maxillary section. It includes a central vault engaging section 12 surrounded by a ridge engaging U-shaped trough 14. An outer side wall 16 is an extension of the trough. The edges of the side wall are shaped to cover the tissue areas and provide relief for functioning musculature and related attachments. For example, the side wall has a notch 18 adapted to provide relief for the labial frenum as well as buccal frenum 20. The posterior extension 22 of the vault 12 is contoured to extend past the border of the hard and soft palate, through the hamular notches. The rear edges 24 of the side walls 16 are shaped to extend superiorly into the post tuberosity area.

The vault engaging section 12 is formed with a central pleat 25 formed along its midsection so as to bisect the trough 14. The pleat extends away from the vault side of the plate so as to avoid interference with the fit of the plate against the vault and tapers in depth from a maximum depth at the posterior border, forming into the vault at the anterior, adjacent to the central area of the trough. The pleat sides form an acute angle relative to one another so that the pleat has a V-shaped cross-section. The pleat allows lateral adjustment of the separation between the two sides of the trough when the plate is elevated in temperature as will be subsequently described.

A handle 26 projects downwardly from the convex side beneath the arch 14 and allows the tray to be inserted and positioned in the patient's mouth without tissue distortion or interference with border molding procedures.

Tissue stops 28 are formed on the concave side of the U-shaped arch 14. These stops consist of raised areas. They act to space the concave surface of the tray from the desired tissue areas to allow room for proper thickness of a final impression material as well as aid in the proper adaptation and/or placement of the tray.

Figure 4:
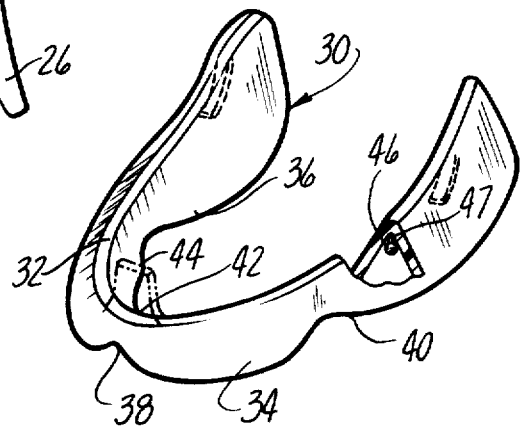
FIG. 4 is a perspective view of a mandibular impression tray forming a second embodiment of the invention, with a section broken away for purposes of illustration.
Figure 5:
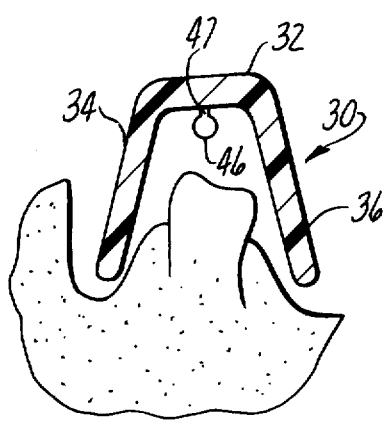
FIG. 5 is a sectional view through a portion of the tray of FIG. 4 in operative position with respect to a dentulous alveolar ridge.
Figure 6:
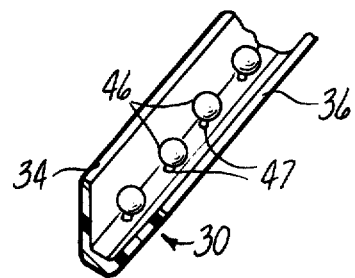
FIG. 6 is a detailed perspective section of a portion of the tray of FIG. 4 illustrating an example of retentive devices.

The mandibular impression tray generally indicated at 30 in FIGS. 4 through 6 represents an alternative embodiment of the invention intended for use with a dentulous arch. Like the maxillary tray of FIGS. 1 through 3 it has a contoured edge relief which makes a close anatomical fit with the desired impression area.

The tray 30 has a generally U-shaped occlusal ridge 32 formed by a continuance of a labial side wall 34 and lingual side wall 36. The side wall 34 has an area of buccal and labial frenum relief 40 formed midway along its sides. The lingual wall 36 has a relieved area 42 for the genioglossus and geniohyoid muscles and is anatomically formed to allow for muscle attachments 44 midway along its length for the anterior attachment of the mylohyoid muscles. At its rear end the tray has extensions which cover the retromolar pad and retromylohyoid fossae. The mandibular tray shown does not employ a handle although handles could be provided in alternate embodiments.

As an alternative to tissue stops the tray 30 has retentive devices 46 formed at spaced points on its concave surface. The structure of these retentive devices is illustrated in the broken-away section of FIG. 4 and the detailed section of FIG. 6. The retentive devices 46 take the form of small spherical balls raised above the surface of the tray 30 in pillars 47. These retentive devices extend out of the concave side of the arch 32. They resist displacement of the final impression material with respect to the tray. They may also act as tissue stops.

The plates 10 and 30 of the present invention are formed of a thermoplastic material having a glass transition temperature above body temperature and below about 135° F. The glass transition temperature of a thermoplastic material is that temperature at which the material changes from its glassy, brittle state to a leathery state characterized by a change in stiffness of several orders of magnitude.

The thermoplastic material used to form the trays is preferably an acrylic and the preferred embodiment of the invention employs a polymer consisting of the reaction product of copolyethyl (methyl) methacrylate with a monomethyl methacrylate. This is formed by mixing copolyethyl (methyl) methacrylate powder and polymethyl methacrylate powder with monomethacrylate liquid, suitable plasticizers, cross-linkers, and accelerators. The formation of other thermoplastic materials having the required mechanical characteristics is well within the skill of practitioners in the plastic art.

In use, after selecting a tray which makes a close fit with the desired impression area and trimming the margins of the tray if necessary, the dentist may warm the tray above its softening point by dipping it in warm water or warming it with an air blower. The tray may be then inserted into the mouth and manually molded to achieve a high degree of conformity to the surrounding tissue area. The width of the tray may be adjusted and the angle of the pleat sides to one another will vary to give up or take slack. The tray will harden within the mouth in a relatively short period of time, i.e., thirty seconds to one minute, depending upon the exact plastic composition used, the temperature to which the tray is softened, and the thickness of the tray. If this hardening occurs before the molding is completed the tray may be removed from the mouth and reheated and the molding continued. After the molding is completed and the tray is fully hardened it may be removed from the mouth without deformation, providing a close approximation to the tissue and surrounding muscle attachments.

After the molding has been completed and tray removed from the mouth, conventional commercially available border molding compounds of the type employed with present customized final impression trays are added to the peripheral borders of the tray. The tray is placed in the mouth again and the border material adjusted to the musculature of the mouth.

The final impression tray thus formed is used in the same manner as a conventional final impression tray. The tray and the border area are filled with a high registration dental impression material such a alginate, permalastic, or silicone and then placed in the mouth to obtain a detailed impression of the mouth tissues. After the detailed impression material sets, the thus completed final impressions are removed and used in a conventional manner.

Since this thermal forming of the thermoplastic, anatomically shaped impression tray may be performed in a single procedure, and the laboratory steps of casting a male model and making a final impression tray from a preliminary impression may be eliminated, both the monetary and time savings of these trays created by the present invention are substantially lower than trays formed by the conventional process.

The embodiments of the invention in which an exclusive property or privilege is claimed are defined as follows:

1. A dental impression tray consisting of a sheet of thermoplastic material having a glass transition temperature between about 100° F. and 135° F. having a contour approximating a section of a patient's oral cavity of which an impression is to be made and peripheral borders shaped to cover the adjacent tissue areas with relief for the functioning musculature and related attachments, whereby the tray may be heated above its glass transition temperature exteriorly of the oral cavity and placed into the patient's mouth at a temperature low enough to not cause discomfort where it can be manually molded to approximate intimacy with that oral section before the tray cools below its glass transition temperature in the mouth of the patient to form a rigid final impression tray which is self-supporting and accurately maintains the molded structure.

2. The dental impression tray of claim 1 in which the thermoplastic is an acrylic.

3. The dental impression tray of claim 2 wherein the acrylic constitutes methylmethacrylate.

4. The dental impression tray of claim 3 wherein the acrylic is a polymer of polymethylmethacrylate and monomethylmethacrylate.

5. The dental impression tray of claim 1 including a handle fixed to or part of the tray at the labial point.

6. The dental impression tray of claim 1 including tissue stops projecting from the concave surface of the tray at spaced points adapted to space the tray with respect to the oral surfaces to be recorded accurately by allowing proper thickness of a final impression material.

7. The dental impression tray of claim 1 including a U-shaped trough having an apex and means depending from the apex of the trough adapted to engage and retain final impression material inserted into the trough.

8. The dental impression tray of claim 7 wherein said means further provide spaced projections adapted to space the tray with respect to the oral surfaces to be recorded thereby insuring proper thickness of the final impression material.

9. The dental impression tray of claim 8 wherein said means comprises a plurality of posts having a generally spherical structure at one end and coupled to the trough apex at the other end.

10. The dental impression tray of claim 1 shaped to contour to a dentulous alveolar ridge.

11. The dental impression tray of claim 1 shaped to contour to an edentulous alveolar ridge.

12. The dental impression tray of claim 1 for a maxillary section having a U-shaped trough adapted to engage an alveolar ridge and a palatal vault engaging section extending from and supported within the trough, the vault having a pleat extending away from the vault engaging side to allow the lateral separation of the opposed trough sides to be adjusted when the tray is heated above its glass transition temperature.

13. The method of forming a final dental impression tray comprising: heating an anatomically shaped thermoplastic impression tray having a glass transition temperature between about 100° F. and 135° F. above its transition temperature exteriorly of the mouth; placing the heated tray into position with respect to the area of which an impression is to be taken and manually molding the tray to conform closely to the anatomy of the mouth.

14. The method of claim 13 including the step of trimming the peripheral borders of the tray to conform to the oral tissues and muscle attachments.

15. The method of claim 13 including the step of adding moldable border material to the peripheral borders of the tray and causing the material to be intimately molded within the mouth.

16. A dental impression tray comprising: a sheet of thermoplastic material which can be molded when heated to a temperature above the temperature encountered in the oral cavity of which an impression is to be made, said sheet having a U-shaped trough adapted to engage an alveolar ridge and a palatal vault engaging section extending from and supported within the trough, said vault section having a pleat extending away from the vault engaging side, whereby the tray may be heated exteriorly of the oral cavity, placed into position relative to the oral section for which an impression is to be made and manually molded to approximate intimacy with that oral section before the tray cools to form a rigid final impression tray which is self-supporting, said pleat allowing the lateral separation of the opposed trough sides to be adjusted to accomodate different oral cavity widths without interfering with the fit of the tray vault section against the palate and aiding in preventing the tray from reverting back to its premolded shape.

17. The dental impression tray of claim 16 wherein said pleat is centrally located along the midsection of the vault section and tapers in depth from a maximum depth at the posterior border and blending into the vault section at the anterior portion.

18. The dental impression tray of claim 16 wherein the thermoplastic material has a glass transition temperature above body temperature and below a temperature which would cause discomfort to the patient when placed into the mouth for molding.

19. The dental impression tray of claim 18 wherein the glass transition temperature of the thermoplastic material is between about 100° F. and 135° F.

20. In the method of forming a final impression of an alveolar ridge including the step of producing a male model of the desired oral tissues from a thermoplastic impression tray, the improvement comprising the steps of:

heating said tray above its glass transition temperature outside of the mouth;

placing the heated tray into position in the patient's mouth with respect to the area of which an impression is to be taken;

manually molding the tray to conform closely to the tissues of the mouth;

allowing the tray to cool below its glass transition temperature while in the patient's mouth;

removing the tray from the mouth;

filling the tray with a dental impression material;

placing the filled try into the mouth to obtain a detailed impression of the mouth tissues;

removing the tray from the mouth; and thereafter, forming a final male model from the impression in the tray, with said tray maintaining its molded structure so as to not disturb the accuracy of the impression.

21. The method of claim 20 wherein said tray has a glass transition temperature above body temperature and below about 135° F.

22. The method of claim 21 which further includes the step of making the impression tray from an acrylic thermoplastic material comprised of a polymer of polymethylmethacrylate and monomethylmethacrylate.

23. The method of claim 20 which further includes the additional step of reheating the tray above its glass transition temperature outside of the mouth and again inserting the tray back into the mouth to finish the molding of the tray around the mouth tissues.

* * * * *